United States Patent [19]

Tanaka et al.

[11] Patent Number: 4,701,465
[45] Date of Patent: Oct. 20, 1987

[54] N-ACYLPYRROLIDINE DERIVATIVE AND SYNTHESIS AND USE THEREOF

[75] Inventors: Takaharu Tanaka; Masayuki Saitoh; Masaki Hashimoto; Naoki Higuchi, all of Osaka, Japan

[73] Assignee: Suntory Limited, Osaka, Japan

[21] Appl. No.: 852,711

[22] Filed: Apr. 16, 1986

[30] Foreign Application Priority Data

Apr. 16, 1985 [JP] Japan .................................. 60-80870

[51] Int. Cl.⁴ ..................... A61K 31/40; C07D 207/08
[52] U.S. Cl. .................................... 514/423; 548/530; 548/533; 548/540
[58] Field of Search ................. 548/533, 540; 514/423

[56] References Cited

U.S. PATENT DOCUMENTS

| 4,128,653 | 12/1978 | Cushman et al. | 514/315 |
| 4,154,937 | 5/1979 | Cushman et al. | 546/221 |
| 4,226,775 | 10/1980 | McEvoy et al. | 548/533 |
| 4,374,847 | 2/1983 | Gruenfeld | 548/430 X |
| 4,439,611 | 3/1984 | Raghu et al. | 548/533 |
| 4,479,963 | 10/1984 | Gruenfeld | 546/256 X |

FOREIGN PATENT DOCUMENTS 0019411 11/1980 European Pat. Off. .

OTHER PUBLICATIONS

Noller, "Chemistry of Organic Compounds", 3rd. ed., 1965, pp. 150, 151, 197, 268; W. B. Saunders, Co., Phila. & London.

The Proceedings of the 1984 Annual Meeting of "The Agricultural Chemical Society of Japan", pp. 752–754.
Agri. Biol. Chem., 42(12), pp. 2417–2419, 1978.

Primary Examiner—Joseph Paul Brust
Attorney, Agent, or Firm—Cushman, Darby & Cushman

[57] ABSTRACT

The present invention relates to N-acylpyrrolidine derivatives of the general formula (I):

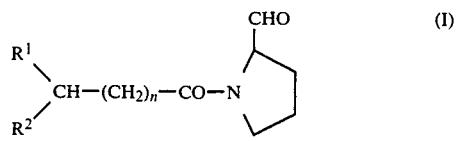

wherein $R^1$ is a hydrogen atom, a $C_{1-4}$ alkyl group or the phenyl group, with the proviso that when $R^1$ is a hydrogen atom, $R^2$ is phenoxy group, benzoyl, the phenyl group, or a phenyl group which is mono-substituted by a halogen atom or a $C_{1-4}$ alkoxy group, and that when $R^1$ is a $C_{1-4}$ alkyl group or the phenyl group, $R^2$ is an aralkyl group of 7 to 10 carbon atoms, a $C_{1-4}$ alkyl group, the phenyl group or a phenyl group mono-substituted by a halogen atom or a $C_{1-4}$ alkoxy group; or $R^1$ and $R^2$ together form an unsubstituted benzylidene group or a benzylidene group which may be mono-substituted by a $C_{1-4}$ alkoxy group; wherein n is an integer of 0 to 5; and pharmaceutical compositions thereof which are useful as anti-amnesic agents.

10 Claims, No Drawings

N-ACYLPYRROLIDINE DERIVATIVE AND SYNTHESIS AND USE THEREOF

BACKGROUND OF THE INVENTION

The present invention relates to a novel compound that exhibits enzyme inhibiting activity against prolyl endopeptidase (EC, 3.4.21.26). The invention also relates to a method for chemical synthesis of such novel compound, as well as its use as a prolyl endopeptidase activity inhibitor and a drug, in particular an anti-amnesic agent, that contains it as the active ingredient.

Prolyl endopeptidase is known to inactivate neurotransmitters such as Substance P, thyrotropin-releasing hormone (TRH) and neurotensin, or vasopressin speculatively associated with memory. Tsuru and Yoshimoto of the Department of Pharmaceutical Sciences, Nagasaki University, found that compounds capable of inhibiting the prolyl endopeptidase activity were effective for preventing experimental amnesia caused in rats by scopolamine. Based on this discovery, they suggested the potential use of prolyl endopeptidase activity inhibitors as anti-amnesic agents (T. Yoshimoto and D. Tsuru, Agr. Biol. Chem. 42, 2417, 1978).

SUMMARY OF THE INVENTION

Motivated by the report of Tsuru and Yoshimoto, the present inventors made various efforts to find novel compounds that exhibited strong anti-amnesic activity and which yet had satisfactorily low toxicity levels. As a result the inventors have found that N-acylpyrrolidine derivatives with anti-prolyl endopeptidase activity having the formula (I) shown below exhibited excellent effects against amnesia. The present invention has been accomplished on the basis of this finding.

DETAILED DESCRIPTION OF THE INVENTION

The N-acylpyrrolidine derivatives of the present invention are represented by the general formula (I):

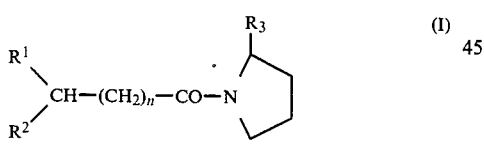

wherein
$R^1$ is hydrogen atom, a lower alkyl group or phenyl group,
$R^3$ is a lower alkyloxycarbonyl group, hydroxymethyl group or formyl group,
when $R^1$ is hydrogen atom, $R^2$ is a substituted or unsubstituted phenyloxy group or phenylcarbonyl group or a substituted phenyl group, and when $R_1$ is a lower alkyl group or phenyl group, $R^2$ is a substituted or unsubstituted phenyl group, a lower alkyl group, an aralkyl group of 7 to 10 carbon atoms or hydroxy group; or $R^1$ and $R^2$ together form a benzylidene group which is unsubstituted or substituted on its aromatic moiety, and
n is an integer of 0 to 5.

Each of $R^1$ and $R^2$ as a lower alkyl group may, for example, be straight or branched alkyl of 1 to 4 carbon atoms such as methyl and i-propyl etc.

When $R^3$ is a lower alkyloxycarbonyl, the lower alkyl moiety in $R^3$ may, for example, have the same meaning as given for $R^1$ and $R^2$ as a lower alkyl.

When $R^2$ is a substituted phenyloxy group or substituted phenyl group, the substituent may, for example, be a halogen atom or a lower alkoxy of 1 to 4 carbon atoms.

When $R^2$ is said aralkyl group or $R^2$ forms a benzylidene group together with $R^1$, their aromatic rings may be substituted by a halogen atom or a lower alkoxy group of 1 to 4 carbon atoms.

The compounds of formula (I) differ greatly from the known 2-oxopyrrolidine anti-amnesic agents such as piracetam or aniracetam in that the former contains a proline residue or a derivative thereof in its structure. Because of this feature, the compounds of formula (I) present extremely low toxicity levels in organisms.

The compounds of formula (I) of the present invention may be synthesized by the following procedures:

(i) the compounds of the formula (Ia)

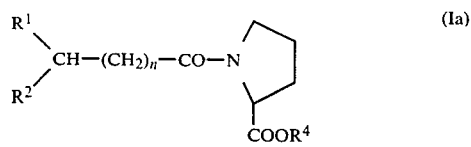

wherein $R^1$, $R^2$ and n have the meanings given above and $R^4$ is hydrogen atom or a lower alkyl group, are obtained by condensation reaction of a carboxylic acid of the formula (II):

wherein $R^1$, $R^2$ and n have the same meanings as given above or a reactive derivative thereof with proline, proline alkylester or salt thereof of the formule (III):

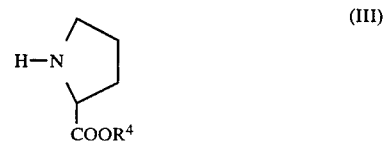

wherein $R^4$ have the meaning given above.

In the condensation reaction, if the starting material is a carboxylic acid of the general formula (II), use of a condensing agent commonly used in peptide synthesis such as N-ethyl-N'N'-dimethylaminopropylcarbodiimide is preferred. Examples of the reactive derivatives of the carboxylic acid of the formula (II) are acid chlorides, acid anhydrides, and active esters of the carboxylic acid. If the starting material is selected from those reactive derivatives, the condensation may be conducted by using a base such as trialkylamine as a condensing agent. Some reactive derivatives of the carboxylic acid may react without any condensing agent being added.

(ii) the compounds of the formula (Ia) may be treated with a reducing agent to give the compounds of the general formula (Ib):

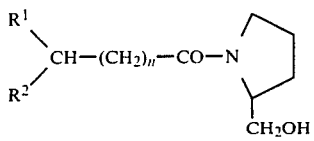

wherein $R^1$, $R^2$ and n have the meanings given above providing that $R^2$ is not phenylcarbonyl.

Any reducing agent can be employed if it does not reduce amides. The preferred reducing agent is sodium borohydride. The reduction is conducted in an ethereal or alcoholic solvent at a temperature ranging from ambient temperature to below 100° C., and preferably between 40° and 70° C.

In a particularly preferred method, a compound of the general formula (Ia) is dissolved together with an excess amount of sodium borohydride in t-butanol or tetrahydrofuran, followed by dropwise addition of methanol under heating. The ratio of t-butanol or tetrahydrofuran to methanol is preferably about 5:1 by volume.

(iii) the compounds of the formula (Ib) thus obtained are then oxidized to give another series of the compunds of the present invention expressed by the general formula (Ic):

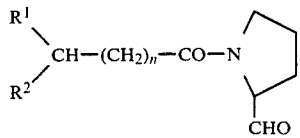

wherein $R^1$, $R^2$ and n have the meanings already given, providing that $R^2$ is not hydroxy group.

(iv) alternatively, the compounds of the present invention expressed by the general formula (I) are also obtained by replacing proline alkylester derivative of the above formula (III) by a 2-formylpyrrolidine derivative, the formyl group of which is protected, and which is expressed by the general formula (IV):

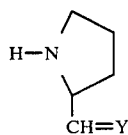

wherein Y is a protective group of aldehyde and this derivative (IV) is condensed with the carboxylic acid of the general formula (II); or a 2-hydroxymethylpyrrolidine, the hydroxy group of which is protected, of the formula (V):

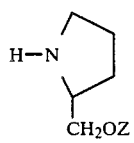

wherein Z is a protective group of hydroxyl group is condensed with carboxylic acid of the general formula (II) and then the protective group is removed by a weak acid or a weak alkaline.

The compound of the invention formed in the reaction mixture may be isolated by an appropriate conventional purification method such as column chromatography, preparative thin layer chromatography or distillation.

The compound of the present invention exerts an inhibitory effect against prolyl endopeptidase. For example, the inhibitory effect of the compounds against this enzyme was examined using z-glycyl-prolyl-$\beta$-naphthylamide as a substrate. As shown later in the experimental example, the compound (I) showed inhibitory activity against prolyl endopeptidase but none at all against papain, bromelain, trypsin, chymotrypsin and thermolysin.

The above inhibitory effect enables the application of the present invention for the purpose of improving brain malfunction including application to amnesia.

The present invention is hereunder described in greater detail by reference to Examples.

EXAMPLE 1

Synthesis of N-(3-phenoxy)propionyl-proline methyl ester (Compound No. 19)

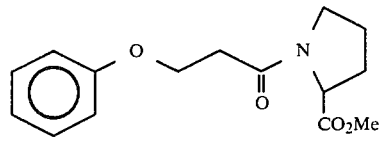

Proline methyl ester hydrochloride (3.4 g), 3-phenoxypropionic acid (3.4 g) and triethylamine (2.8 ml) were suspended in dry methylene chloride (30 ml). To the cooled suspension, WSCD HCl (N-ethyl-N',N'-dimethylaminopropyl-carbodiimide hydrochloride) (3.9 g) was added. Under cooling, the mixture was stirred for 1 hour, and after allowing the mixture to warm to room temperature, it was again stirred for 18 horus. The stirred mixture was washed successively with water, 1N HCl, water, saturated aqueous sodium bicarbonate and brine. After drying over anhydrous magnesium sulfate, the solvent was distilled off under vacuum. The resulting crude product was purified by medium-pressure liquid column chromatography on silica gel (solvent: chloroform) to obtain the end compound as an oil (3.7 g).

EXAMPLE 2

Synthesis of N-(3-phenoxy)propionyl-prolinol (Compound No. 20)

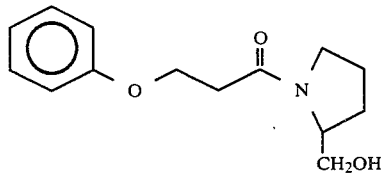

A mixture of N-(3-phenoxy)propionyl-proline methyl ester (2.8 g) and sodium borohydride (950 mg) was suspended in tertiary butyl alcohol (40 ml). To the stirred suspension, dry methanol (8 ml) was added dropwise under reflux. Thereafter, the mixture was stirred under reflux for 1 hour. The heated mixture was cooled to room temperature and water (10 ml) was added under cooling with ice. Methanol and tertiary butyl alcohol were distilled off under vacuum and the residue was subjected to extraction with ethyl acetate. The extract was washed with brine and dried over anhydrous magnesium sulfate. The solvent was distilled off under vacuum and the resulting crude product was purified by medium-pressure liquid column chromatography on silica gel (solvent: chloroform) to obtain the end compound as an oil (2.3 g).

EXAMPLE 3

Synthesis of N-(3-phenoxy)propionyl-prolinal (Compound No. 21)

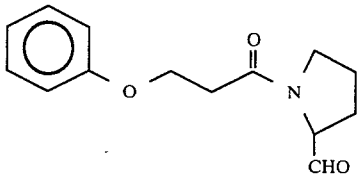

A mixture of N-(3-phenoxy)propionyl-prolinol (1.4 g) and triethylamine (1.7 g) was dissolved in anhydrous dimethyl sulfoxide (16 ml), and to the stirred solution, a solution (16 ml) of sulfur trioxide-pyridine complex (2.6 g) in dimethyl sulfoxide was added. After stirring the mixture for 10 minutes, the reaction solution was poured into iced water (150 ml) and subjected to extraction with ethyl acetate. The extract was washed successively with 10% aqueous citric acid, water, saturated aqueous sodium bicarbonate and brine, and dried over anhydrous magnesium sulfate. After distilling off the solvent under vacuum, the resulting crude product was purified by medium-pressure liquid column chromatography on silica gel (solvent: chloroform) to obtain the end compound as an oil (1.2 g).

The analytical data for the compounds obtained in Examples 1 to 3 are listed in Table 1. The other compounds listed in Table 1 were also obtained by processes similar to the above examples from the corresponding starting compounds.

TABLE 1

| Compound | Molecular formula | $[\alpha]_D$ | IR $\nu_{max}^{neat}$ cm$^{-1}$ | H—NMR ($\delta$, CDCl$_3$) | MS (m/z) |
| --- | --- | --- | --- | --- | --- |
| SUAM-1032 (No. 1) | $C_{15}H_{19}NO_4$ (277) | $[\alpha]_D^{21}$ $-64.61°$ (c = 0.89, CHCl$_3$) | 2960, 2880, 2840, 1740, 1650, 1500, 1430, 1250, 1030, 820 | 1.85–2.15(4H,m), 3.48–3.62(4H,m), 3.69, 3.75(3H each, both s), 4.49(1H,m), 6.74–7.25(4H,m) | 277 (M$^+$) |
| SUAM-1026 (No. 2) | $C_{16}H_{21}NO_4$ (291) | $[\alpha]_D^{23}$ $-60.82°$ (c = 1.46, CHCl$_3$) | 2960, 2880, 2840, 1740, 1650, 1500, 1430, 1250, 1030, 830 | 1.85–2.25(4H,m), 2.40, 3.08(4H,m), 3.47(2H,m), 3.70, 3.74(3H each, both s), 4.47(1H,m), 6.70–7.20(4H,m) | 291 (M$^+$) |
| SUAM-1034 (No. 3) | $C_{17}H_{23}NO_4$ (305) | $[\alpha]_D^{22}$ $-48.87°$ (c = 1.33, CHCl$_3$) | 2980, 2950, 2880, 1750, 1640, 1500, 1430, 1250, 1030, 840 | 1.83–2.20(6H,m), 2.63–2.87(2H,m), 3.18–3.50(2H,m), 3.69, 3.83(3H each, both s), 3.56(2H,m), 3.51(1H,m), 6.89, 7.96(2H each, both d, J=9Hz) | 305 (M$^+$) |
| SUAM-1040 (No. 4) | $C_{14}H_{19}NO_3$ (249) | $[\alpha]_D^{30}$ $-46.99°$ (c = 0.83, CHCl$_3$) | 3380, 2950, 1610, 1500, 1440, 1250, 1030, 820 | 1.69–2.02(4H,m), 3.33–3.60(4H,m), 3.57, 3.72(3H each, both d), 4.10(1H, m), 5.09(1H,m), 6.72–7.22(4H,m) | 249 (M$^+$) |

TABLE 1-continued

| Compound | | Molecular formula | $[\alpha]_D$ | IR $\nu_{max}^{neat}$ cm$^{-1}$ | H—NMR ($\delta$, CDCl$_3$) | MS (m/z) |
|---|---|---|---|---|---|---|
| SUAM-1041 (No. 5) | 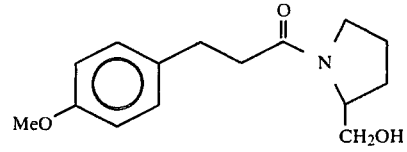 | C$_{15}$H$_{21}$NO$_3$ (263) | $[\alpha]_D^{26}$ $-37.45°$ (c = 1.02, CHCl$_3$) | 3380, 2950, 1610, 1500, 1440, 1250, 1030, 830 | 1.62–2.02(4H,m), 2.36–3.05(4H,m), 3.19–3.67(4H,m), 3.72(3H,s), 4.12(1H,m), 5.12(1H,m), 6.70–7.18(4H,m) | 263 (M$^+$) |
| SUAM-1042 (No. 6) | 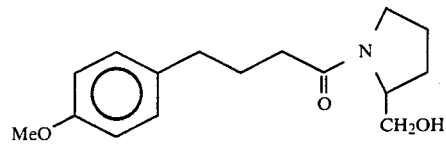 | C$_{16}$H$_{23}$NO$_3$ (277) | | 3380, 2950, 1610, 1500, 1440, 1250, 1030, 840 | 1.63–2.37(10H,m), 3.25–3.67(4H,m), 3.37(3H,s), 4.13, 4.74(1H each, both m), 6.61–7.30(4H,m) | 277 (M$^+$) |
| SUAM-1049 (No. 7) | 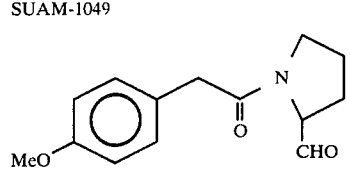 | C$_{14}$H$_{17}$NO$_3$ (247) | $[\alpha]_D^{25}$ $-106.83°$ (c = 0.82, CHCl$_3$) | 2970, 2880, 1730, 1630, 1500, 1430, 1250, 1030, 820 | 1.95(4H,m), 3.55(2H,m), 3.65(3H,s), 3.78(3H,s), 4.45(1H,m), 6.81–7.24(4H,m), 9.46, 9.51(total 1H, both d, J=2Hz) | 247 (M$^+$) |
| SUAM-1050 (No. 8) | 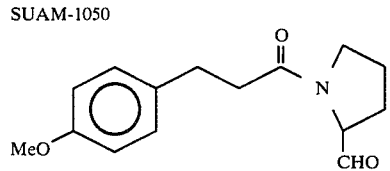 | C$_{15}$H$_{19}$NO$_3$ (261) | $[\alpha]_D^{30}$ $-88.62°$ (CHCl$_3$, (C = 1.09) | 2950, 2870, 1730, 1640, 1500, 1430, 1250, 1030, 830 | 1.60–1.86(4H,m), 2.38(2H,m), 2.71 (2H,m), 3.21(2H,m), 3.54(3H,s), 4.11 (1H,m), 6.56–6.98 (4H,m), 9.20, 9.21 (total 1H, both d, J=2Hz) | 261 (M$^+$) |
| SUAM-1051 (No. 9) | 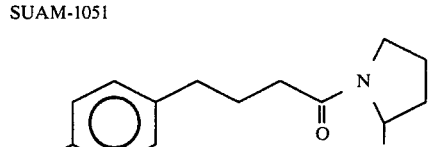 | C$_{16}$H$_{21}$NO$_3$ (275) | $[\alpha]_D^{24}$ $-44.21°$ (c = 0.19, CHCl$_3$) | 2970, 2870, 1730, 1630, 1500, 1440, 1250, 1170, 1030, 840 | 2.02(6H,m), 2.87 (2H,m), 3.36(2H,m), 3.72(2H,m), 3.87 (3H,s), 4.44(1H,m), 6.93, 7.97(2H each, both d, J=9Hz), 9.51, 9.68(total 1H, both d, J=2Hz) | 275 (M$^+$) |
| SUAM-1033 (No. 10) | 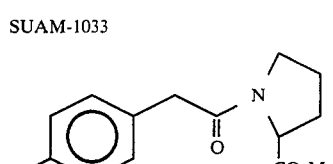 | C$_{14}$H$_{16}$NO$_3$Cl (281.5) | $[\alpha]_D^{24}$ $-55.85°$ (c = 1.06, CHCl$_3$) | 2950, 2880, 1740, 1650, 1430, 1200, 810, 750 | 1.78–2.27(4H,m), 3.42–3.63(4H,m), 3.69(3H,s), 4.50(1H,m), 7.22(4H,s) | 281, 283 (M$^+$) |
| SUAM-1045 (No. 11) | 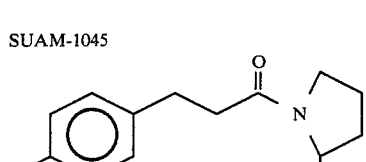 | C$_{15}$H$_{18}$NO$_3$Cl (295.5) | $[\alpha]_D^{29}$ $-58.78°$ (c = 0.74, CHCl$_3$) | 2950, 2880, 1740, 1640, 1430, 1200, 830, 790 | 1.88–2.14(4H,m), 2.41–3.10(4H,m), 3.48(2H,m), 3.70(3H,s), 4.48(1H,m), 7.17(4H,brs) | 295, 297 (M$^+$) |

TABLE 1-continued

| Compound | Molecular formula | $[\alpha]_D$ | IR $\nu_{max}^{neat}$ cm$^{-1}$ | H—NMR ($\delta$, CDCl$_3$) | MS (m/z) |
|---|---|---|---|---|---|
| SUAM-1058 (No. 12) | C$_{16}$H$_{20}$NO$_3$Cl (309.5) | $[\alpha]_D^{27}$ −54.22° (c = 0.45, CHCl$_3$) | 2950, 2870, 1740, 1640, 1430, 1200, 840, 800 | 1.77–2.78(10H,m), 3.45(2H,m), 3.71(3H,s), 4.48(1H,m), 7.17(4H,m) | 309, 311 (M$^+$) |
| SUAM-1043 (No. 13) | C$_{13}$H$_{16}$NO$_2$Cl (253.5) | $[\alpha]_D^{29}$ −53.79° (c = 0.95, CHCl$_3$) | 3380, 2960, 2870, 1620, 1430, 810, 750 | 1.68–2.15(4H,m), 3.34–3.71(6H,m), 3.60(3H,s), 4.12(1H,m), 4.94(1H,m), 7.20(4H,brs) | 253, 255 (M$^+$) |
| SUAM-1048 (No. 14) | C$_{14}$H$_{18}$NO$_2$Cl (267.5) | $[\alpha]_D^{30}$ −33.79° (c = 1.03, CHCl$_3$) | 3400, 2980, 2870, 1620, 1440, 820, 750 | 1.65–2.12(4H,m), 2.38–3.06(4H,m), 3.22–3.63(4H,m), 4.14(1H,m), 5.10(1H,m), 7.14(4H,brs) | 267, 269 (M$^+$) |
| SUAM-1063 (No. 15) | C$_{15}$H$_{20}$NO$_2$Cl (281.5) | $[\alpha]_D^{30}$ −43.81° (c = 0.42, CHCl$_3$) | 3400, 2960, 2880, 1620, 1440, 830, 800, 760 | 1.71–2.77(10H,m), 3.29–3.65(4H,m), 4.16(1H,m), 5.01(1H,m), 7.16(4H,m) | 281, 283 (M$^+$) |
| SUAM-1052 (No. 16) | C$_{13}$H$_{14}$NO$_2$Cl (251.5) | $[\alpha]_D^{25}$ −32.93° (c = 1.50, CHCl$_3$) | 2980, 2880, 1730, 1630, 1440, 810, 750 | 1.93(4H,m), 3.45–3.65(4H,m), 4.44(1H,m), 7.22(4H,m), 7.47(1H,d,J=2Hz) | 251, 253 (M$^+$) |
| SUAM-1053 (No. 17) | C$_{14}$H$_{16}$NO$_2$Cl (265.5) | $[\alpha]_D^{30}$ −43.41° (c = 1.23, CHCl$_3$) | 2980, 2880, 1730, 1630, 1430, 820 | 1.93(4H,m), 2.59(2H,m), 2.89(2H,m), 3.43(2H,m), 4.41(1H,m), 7.18(4H,m), 9.46(1H,d,J=2Hz) | 265, 267 (M$^+$) |
| SUAM-1064 (No. 18) | C$_{15}$H$_{18}$NO$_2$Cl (279.5) | $[\alpha]_D^{28}$ −69.86° (CHCl$_3$, c = 1.40) | 2980, 2880, 1730, 1640, 1430, 800, 760 | 1.82(6H,m), 2.21(2H,m), 2.54(2H,m), 3.35(2H,m), 4.27(1H,m), 7.05(4H,m), 9.35(1H,d,J=2Hz) | 279, 281 (M$^+$) |

TABLE 1-continued

| Compound | Molecular formula | $[\alpha]_D$ | IR $\nu_{max}^{neat}$ cm$^{-1}$ | H—NMR ($\delta$, CDCl$_3$) | MS (m/z) |
|---|---|---|---|---|---|
| SUAM-1014 (No. 19) | C$_{15}$H$_{19}$NO$_4$ (277) | $[\alpha]_D^{30}$ −68.55° (c = 0.62, CHCl$_3$) | $\nu_{max}^{KBr}$ cm$^{-1}$: 2950, 1740, 1640, 1440, 1240, 1200, 1030, 760, 690 | 1.76–2.13(4H,m), 2.77(2H,m), 2.77 (2H,t,J=7.2Hz), 3.67(3H,s), 4.27 (2H,t,J=7.2Hz), 4.48(1H,m), 6.78–7.34(5H,m) | 277 (M$^+$) |
| SUAM-1015 (No. 20) | C$_{14}$H$_{19}$NO$_3$ (249) | $[\alpha]_D^{24}$ −47.91° (c = 1.34, CHCl$_3$) | 3400, 2980, 2880, 1620, 1450, 1250, 1060, 1040, 770 | 1.64–2.18(4H,m), 2.77(2H,t,J=7.2Hz), 3.41–3.78(4H,m), 4.28(2H,t,J=7.2Hz), 4.20(1H,m), 4.83(1H,m), 6.78–7.35(5H,m) | 249 (M$^+$) |
| SUAM-1019 (No. 21) | C$_{14}$H$_{17}$NO$_3$ (247) | $[\alpha]_D^{31}$ −89.45° (c = 2.75, CHCl$_3$) | 2980, 2880, 1730, 1630, 1440, 1240, 1040, 760, 700 | 1.80–2.17(4H,m), 2.84(2H,t,J=7.2Hz), 3.64(2H,m), 3.34(2H,t,J=7.2Hz), 4.48(1H,m), 6.83–7.37(5H,m), 9.55, 9.63(total 1H, both d, J=2Hz) | 247 (M$^+$) |
| SUAM-1038 (No. 22) | C$_{21}$H$_{23}$NO$_3$ (337) | $[\alpha]_D^{22}$ −61.78° (c = 0.45, CHCl$_3$) | 3020, 2950, 2870, 1740, 1640, 1430, 1200, 750, 700 | 1.72–2.10(4H,m), 3.01(2H,d,J=7.2Hz), 3.23–3.42(2H,m), 3.59(3H,s), 4.37(1H,m), 4.68(1H,t,J=7.2Hz), 7.20(10H,m) | 337 (M$^+$) |
| SUAM-1061 (No. 23) | C$_{20}$H$_{23}$NO$_2$ (309) | $[\alpha]_D^{30}$ −20.87° (c = 0.46, CHCl$_3$) | 3380, 3020, 2970, 2870, 1620, 1450, 1050, 750, 700 | 1.52–1.97(4H,m), 3.01(2H,d,J=7.2Hz), 3.16–3.56(4H,m), 4.01(1H,m), 4.65(1H,t,J=7.2Hz), 4.65(1H,m), 7.22(10H,s) | 309 (M$^+$) |
| SUAM-1065 (No. 24) | C$_{20}$H$_{21}$NO$_2$ (307) | $[\alpha]_D^{25}$ −83.24° (c = 2.59, CHCl$_3$) | 3020, 2970, 2880, 1730, 1640, 1450, 750, 700 | 1.70–1.93(4H,m), 3.06(2H,d,J=7.2Hz), 3.35(2H,m), 4.27(1H,m), 4.64(1H,t,J=7.2Hz), 7.25(10H,s), 9.24(1H,d,J=2Hz) | 307 (M$^+$) |

TABLE 1-continued

| Compound | Molecular formula | $[\alpha]_D$ | IR $\nu_{max}^{neat}$ cm$^{-1}$ | H—NMR ($\delta$, CDCl$_3$) | MS (m/z) |
|---|---|---|---|---|---|
| SUAM-1039 (No. 25) | C$_{16}$H$_{21}$NO$_3$ (275) | $[\alpha]_D^{29}$ $-61.47°$ (c = 0.75, CHCl$_3$) | 2970, 2880, 1740, 1640, 1420, 1200, 740, 720, 700 | 0.85(3H,t,J=7.2Hz), 1.55-2.09(6H,m), 3.15-3.55(3H,m), 3.58, 3.68(total 3H, both s), 4.38 (1H,m), 7.21(5H,s) | 275 (M$^+$) |
| SUAM-1062 (No. 26) | C$_{15}$H$_{21}$NO$_2$ (247) | $[\alpha]_D^{30}$ $-33.41°$ (c = 0.88, CHCl$_3$) | 3400, 2970, 2880, 1620, 1430, 1050, 730, 700 | 0.87(3H,t,J=7.2Hz), 1.54-2.21(6H,m), 3.20-3.70(5H,m), 4.20(1H,m), 5.01(1H,m), 7.27(5H,s) | 248 (M + H)$^+$ |
| SUAM-1066 (No. 27) | C$_{15}$H$_{19}$NO$_2$ (245) | $[\alpha]_D^{31}$ $-81.45°$ (c = 2.34, CHCl$_3$) | 2970, 2880, 1730, 1640, 1420, 730, 700 | 0.83(3H,t,J=7.2Hz), 1.53-2.20(6H,m), 3.20-3.76(3H,m), 4.35(1H,m), 7.24(5H,s), 9.29, 9.49(total 1H, both d, J=2Hz) | 245 (M$^+$) |
| SUAM-1046 (No. 28) | C$_{16}$H$_{19}$NO$_4$ (289) | $[\alpha]_D^{24}$ $-57.38°$ (c = 0.84, CHCl$_3$) | 2970, 2880, 1740, 1680, 1640, 1430, 1200, 740, 680 | 1.79-2.27(4H,m), 2.53-2.98(2H,m), 3.20-3.51(2H,m), 3.52-3.70(2H,m), 3.67(3H,s), 4.49(1H,m), 7.32-7.51(3H,m), 7.83-8.03(2H,m) | 290 (M + H)$^+$ |
| SUAM-1047 (No. 29) | C$_{15}$H$_{21}$NO$_3$ (263) | $[\alpha]_D^{30}$ $-46.84°$ (c = 0.57, CHCl$_3$) | 3380, 2950, 2870, 1610, 1440, 1050, 760, 700 | 1.66-2.51(8H,m), 3.25-3.56(4H,m), 4.01(1H,m), 4.20(3H,m), 7.27(5H,s) | 264 (M + H)$^+$ |
| SUAM-1055 (No. 30) | C$_{15}$H$_{17}$NO$_3$ (259) | $[\alpha]_D^{28}$ $-82.99°$ (c = 1.47, CHCl$_3$) | 2980, 2870, 1720, 1680, 1630, 1440, 750, 690 | 1.73-2.10(4H,m), 2.71(2H,m), 3.32(2H,m), 3.51(2H,m), 4.34(1H,m), 7.35-7.44(3H,m), 7.87-7.97(2H,m), 9.42, 9.58(total 1H, both d, J=2Hz) | 260 (M + H)$^+$ |
| SUAM-1036 (No. 31) | C$_{19}$H$_{27}$NO$_3$ (317) | $[\alpha]_D^{27}$ $-104.27°$ (c = 0.75, CHCl$_3$) | 2950, 2870, 1740, 1640, 1430, 1190, 1170, 750, 700 | 0.83-1.02(6H,m), 1.73-2.86(10H,m), 3.30-3.50(2H,m), 3.70, 3.83(total 3H, both s), 4.53(1H,s), 7.17, 7.22(total 5H, both s) | 318 (M + H)$^+$ |

TABLE 1-continued

| Compound | | Molecular formula | $[\alpha]_D$ | IR $\nu_{max}^{neat}$ cm$^{-1}$ | H—NMR (δ, CDCl$_3$) | MS (m/z) |
|---|---|---|---|---|---|---|
| SUAM-1060 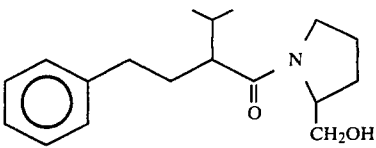 (No. 32) | | C$_{18}$H$_{27}$NO$_2$ (289) | $[\alpha]_D^{27}$ −37.61° (c = 0.88, CHCl$_3$) | 3390, 2950, 2860, 1610, 1440, 1030, 750, 700 | 0.83-1.02(6H,m), 1.48-2.65(10H,m), 3.17-3.37(2H,m), 3.52-3.67(2H,m), 4.22(1H,m), 5.22(1H,m), 7.29(5H,s) | 290 (M + H)$^+$ |
| SUAM-1068 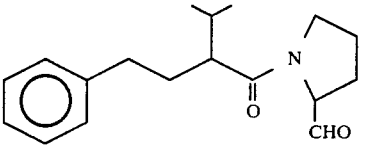 (No. 33) | | C$_{18}$H$_{25}$NO$_2$ (287) | $[\alpha]_D^{24}$ −69.17° (c = 1.2, CHCl$_3$) | 2960, 2870, 1730, 1630, 1440, 750, 700 | 0.91(6H,t,J=7Hz), 1.70-2.77(10H,m), 3.17-3.66(2H,m), 4.45(1H,m), 7.16, 7.20(total 5H, both s), 9.51, 9.54(total 1H, both d, J=2Hz) | 288 (M + H)$^+$ |
| SUAM-1069 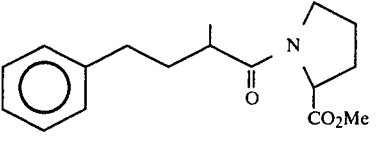 (No. 34) | | C$_{17}$H$_{23}$NO$_3$ (289) | $[\alpha]_D^{29}$ −58.81° (c = 0.59, CHCl$_3$) | 2980, 2950, 2870, 1740, 1640, 1430, 1200, 750, 700 | 1.11, 1.16(total 3H,d,J=6.6Hz), 1.56-2.80(9H,m), 3.30-3.58(2H,m), 3.67, 3.71(total 3H, both s), 4.50(1H,m), 7.16, 7.21(total 5H, both s) | 289 (M$^+$) |
| SUAM-1070 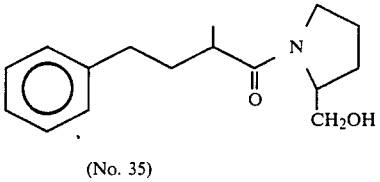 (No. 35) | | C$_{16}$H$_{25}$NO$_2$ (261) | $[\alpha]_D^{30}$ −37.33° (c = 0.45, CHCl$_3$) | 3400, 2970, 2880, 1620, 1440, 1050, 750, 700 | 1.11, 1.16(total 3H, both d,J=6.6Hz), 1.55-2.95(9H,m), 3.16-3.68(4H,m), 4.20(1H,m), 5.21(1H,m), 7.17(5H,s) | 262 (M + H)$^+$ |
| SUAM-1071 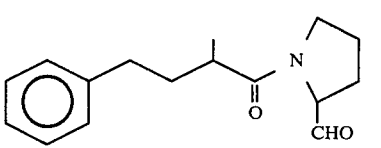 (No. 36) | | C$_{16}$H$_{21}$NO$_2$ (259) | $[\alpha]_D^{25}$ −62.79° (c = 1.36, CHCl$_3$) | 2970, 2870, 1730, 1630, 1430, 750, 700 | 1.11, 1.16(total 3H, both d, J= 6.6Hz), 1.60-2.72 (9H,m), 3.30-3.52 (2H,m), 4.52(1H,m), 7.18(5H,m), 9.42, 9.47(total 1H, both d, J=2Hz) | 260 (M + H)$^+$ |
| SUAM-1025 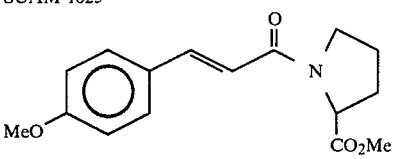 (No. 37) | | C$_{16}$H$_{19}$NO$_4$ (289) | $[\alpha]_D^{28}$ −56.45° (c = 1.07, CHCl$_3$) | 2970, 2900, 1740, 1640, 1600, 1500, 1430, 1200, 820 | 1.86-2.44(4H,m), 3.71, 3.79(3H each, both s), 3.61-3.82(2H,m), 4.60(1H,m), 6.56(1H,d,J=15Hz), 6.76-7.52(4H,m), 7.65(1H,d,J=15Hz) | 289 (M$^+$) |
| SUAM-1044 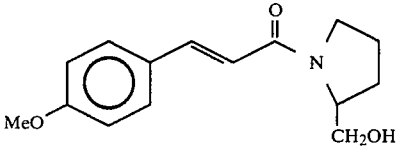 (No. 38) | | C$_{15}$H$_{19}$NO$_3$ (261) | $[\alpha]_D^{27}$ −42.77° (c = 0.94, CHCl$_3$) | 3360, 2970, 2880, 1640, 1600, 1500, 1430, 1240, 820 | 1.71-2.12(4H,m), 3.57-3.82(4H,m), 3.79(3H,s), 4.26(1H,m), 5.34(1H,m), 6.55(1H,d,J=15Hz), 6.76-7.52(4H,m), 7.65(1H,d,J=15Hz) | 262 (M + H)$^+$ |

TABLE 1-continued

| Compound | Molecular formula | $[\alpha]_D$ | IR $\nu_{max}^{neat}$ cm$^{-1}$ | H—NMR ($\delta$, CDCl$_3$) | MS (m/z) |
|---|---|---|---|---|---|
| SUAM-1054 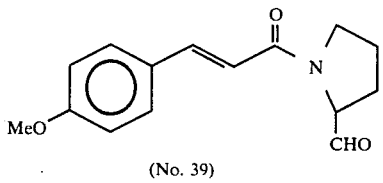 (No. 39) | C$_{15}$H$_{17}$NO$_3$ (259) | $[\alpha]_D^{31}$ (c = 1.14, CHCl$_3$) | 2970, 2880, 1730, 1640, 1600, 1500, 1430, 1240, 820 | 1.85(4H,m), 3.64(3H,s), 3.30-3.52(2H,m), 4.35(1H,m), 6.49(1H,d,J=16Hz), 6.68-7.38(4H,m), 7.53(1H,d,J=16Hz), 9.41(1H,d,J=2Hz) | 259 (M$^+$) |
| SUAM-1087 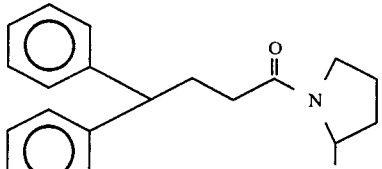 (No. 40) | C$_{22}$H$_{25}$NO$_3$ (351) | $[\alpha]_D^{27}$ −50.00° (c = 0.23, CHCl$_3$) | 3020, 2940, 2870, 1740, 1640, 1420, 1190, 1160, 740, 700 | 1.87-2.14(4H,m), 2.23-2.47(4H,m), 3.25(2H,m), 3.69(3H,s), 3.96(1H,m), 4.44(1H,m), 7.20(10H,m) | 351 (M$^+$) |
| SUAM-1088 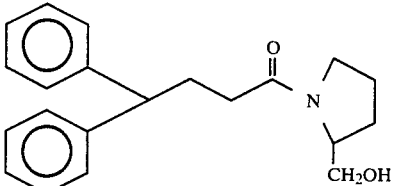 (No. 41) | C$_{21}$H$_{25}$NO$_2$ (323) | $[\alpha]_D^{22}$ −37.74° (c = 0.53, CHCl$_3$) | 3350, 2950, 2870, 1600, 1440, 1050, 750, 700 | 1.57-1.81(4H,m), 2.12-2.48(4H,m), 3.18(2H,m), 3.53(2H,m), 4.00(2H,m), 5.06(1H,m), 7.21(10H,s) | 324 (M + H)$^+$ |
| SUAM-1090 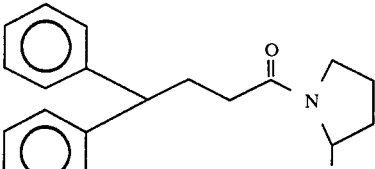 (No. 42) | C$_{21}$H$_{23}$NO$_2$ (321) | $[\alpha]_D^{25}$ −73.86° (c = 1.14, CHCl$_3$) | 2970, 2870, 1720, 1640, 1440, 740, 700 | 1.70-2.02(4H,m), 2.27-2.57(4H,m), 3.21(2H,m), 2.99(1H,t,J=7.2Hz), 4.37(1H,m), 7.24(10H,s), 9.42(1H,d,J=2Hz) | 321 (M$^+$) |

EXAMPLE 4

Measurement of anti-prolyl endopeptidase activity

The method of Yoshimoto and Tsuru (T. Yoshimoto and D. Tsuru, Agr. Biol. Chem. 42, 2417, 1978) was used to measure the anti-prolyl endopeptidase activities of compounds of the present invention. A mixture of 0.0025M Z-glycyl-proline-$\beta$-naphthylamide (0.25 ml), 0.1M phosphate buffer (pH, 7.06; 0.99 ml) and a solution of a particular anti-prolyl endopeptidase compound (0.01 ml) was incubated in a test tube at 37° C. for 3 minutes. Thereafter, 0.1 ml of a solution of prolyl endopeptidase (0.2 U/ml) was added and the mixture was heated at 35° C. for 10 minutes. After the reaction, 2.0 ml of Triton X-100 in 1M acetate buffer (pH, 4.0) was added to the reaction mixture until the final concentration of the surfactant was 10%. The mixture was left at room temperature for 15 minutes and the absorbance (a) at 410 nm was measured.

A sample for a blind test was prepared by using the buffer instead of the anti-prolyl endopeptidase compound and its absorbance (b) was also measured. The percent inhibition of prolyl endopeptidase was calculated by the formula: $((b-a)/b) \times 100$, and the amount of a specific compound to achieve 50% inhibition IC$_{50}$) was determined. The results are shown in Table 2.

TABLE 2

| Compound No. | IC$_{50}$ ($\mu$g/test tube) |
|---|---|
| (1) | 80 |
| (2) | 51 |
| (3) | 180 |
| (7) | 3.0 |
| (8) | 1.0 |
| (9) | 0.05 |
| (10) | 72 |
| (11) | 30 |
| (12) | 50 |
| (16) | 0.5 |
| (17) | 1.0 |
| (18) | 1.5 |
| (19) | 60 |
| (21) | 2.5 |
| (22) | 250 |
| (24) | 0.1 |
| (25) | 510 |

TABLE 2-continued

| Compound No. | IC$_{50}$ (μg/test tube) |
| --- | --- |
| (27) | 0.2 |
| (28) | 200 |
| (30) | 0.1 |
| (31) | >200 |
| (33) | >5 |
| (34) | 80 |
| (36) | 1.0 |
| (37) | 80 |
| (39) | 0.2 |
| (42) | 0.35 |

EXAMPLE 5

Measurement of preventive effect against experimental amnesia caused in rats by scopolamine (intraperitoneal administration)

Several of the anti-prolyl endopeptidase compounds of the present invention were checked for their ability to prevent the inhibition of long-term memory fixation by scopolamine. Solutions of physiological saline that contained selected compounds of the present inventions in an amount of 1 mg/kg were administered intraperitoneally to Wister male rats (100–120 g). One hour after the administration, electric shocks were applied to the rats so that they would acquire passive avoidance learning. Immediately thereafter, scopolamine was administered intraperitoneally to each rat in an amount of 3 mg per kg of body weight.

The result of the test was assessed both 24 hours and 48 hours after the administration of scopolamine. The number of amnesic rats and of sound rats was counted for both the control group (rats which were not given the test compounds but to which scopolamine and physiological saline alone were administered intraperitoneally) and the treated group (rats to which both the test compound and scopolamine were administered). The results are shown in Table 3. Among the tested compounds, SUAM 1051, SUAM 1055 and SUAM 1065 showed particularly remarkable effects.

The present invention also relates to an anti-amnesic agent useful for the treatment of diseases originating from organic disorders in the brain. The anti-amnesic agent comprises at least one compound of the formula (I) together with a pharmaceutically acceptable carrier.

The formulation of the agent of the invention includes either solid formulations such as capsules, tablets and powders or a liquid formulations such as elixirs, syrups and suspensions for oral administration. Alternatively, the active compounds (I) may be formulated as injections or suppositories.

The carrier included in the agent of the invention may be selected from pulverulent solid carriers such as lactose, saccharose, dextrose, mannitol, sorbitol, cellulose, and glycine etc.

The agent of the invention may further contain a lubricant, a binder or a disintegrater. Examples of lubricant are silicon dioxide, talc, magnesium stearate and polyethylene glycol. Examples of binder are starch, gelatin, tragacanth, methyl cellulose and polyvinyl pyrrolidone. Examples of disintegrator are starch and agar etc.

The active ingredient (I) of the agent of the invention is orally administered to an adult patient in a dose of 10 to 4000 mg, preferably 100 to 1000 mg/day, or administered parenterally in a dose of 1 to 2000 mg, preferably 50 to 500 mg/day. The dose may be varied depending on the disease, age, weight, or condition of the patient or the formulation of the drugs.

Formulation 1

| Ingredient | Part |
| --- | --- |
| Compound of the formula (I) | 10 |
| Lactose | 75 |
| Magnesium oxide (MgO >96%) | 15 |

The ingredients are mixed thoroughly, and tablets or capsules are formulated from the mixture.

TABLE 3

Amnesia test with rats (intraperitoneal administration)

| | | | Learning | | | Avoidance time (sec.) | | Pharmacological effect | |
| --- | --- | --- | --- | --- | --- | --- | --- | --- | --- |
| Sample | Drug administration after learning | No. of rats | Initial avoidance time (sec.) | No. of avoidances during learning | Total learning time (sec.) | 24 hrs. later | 48 hrs. later | No. of amnesic rats/No. of rats tested | percentage amnesia |
| physiological saline | physiological saline | 12 | 2.3 | 1.7 | 110.0 | 211.4 | 225.0 | 3/12 | 25% |
| physiological saline | scopolamine (3 mg/kg i.p.) | 13 | 3.5 | 2.5 | 110.0 | 132.5 | 177.0 | 9/13 | 69% |
| SUAM1050 (1 mg/kg i.p.) | scopolamine (3 mg/kg i.p.) | 10 | 2.6 | 2.5 | 110.0 | 198.2 | 203.5 | 5/10 | 50% |
| SUAM1051 (1 mg/kg i.p.) | scopolamine (3 mg/kg i.p.) | 10 | 3.1 | 2.0 | 110.0 | 300.0 | 300.0 | 0/10 | 0% |
| SUAM1052 (1 mg/kg i.p.) | scopolamine (3 mg/kg i.p.) | 10 | 3.2 | 2.7 | 110.0 | 223.1 | 214.8 | 3/10 | 30% |
| SUAM1054 (1 mg/kg i.p.) | scopolamine (3 mg/kg i.p.) | 10 | 2.0 | 1.9 | 110.0 | 204.5 | 199.7 | 5/10 | 50% |
| SUAM1055 (1 mg/kg i.p.) | scopolamine (3 mg/kg i.p.) | 10 | 3.5 | 1.7 | 110.0 | 300.0 | 300.0 | 0/10 | 0% |
| SUAM1065 (1 mg/kg i.p.) | scopolamine (3 mg/kg i.p.) | 10 | 2.9 | 2.0 | 110.0 | 284.6 | 267.2 | 1/10 | 10% |
| SUAM1066 (1 mg/kg i.p.) | scopolamine (3 mg/kg i.p.) | 10 | 3.7 | 1.5 | 110.0 | 268.4 | 205.4 | 3/10 | 30% |
| SUAM1090 (1 mg/kg i.p.) | scopolamine (3 mg/kg i.p.) | 10 | 3.4 | 2.2 | 110.0 | 232.8 | 202.36 | 4/10 | 40% |

Formulation 2

| Ingredient | Part |
|---|---|
| Compound of the formula (I) | 45 |
| Starch | 15 |
| Lactose | 40 |

The above ingredients are mixed thoroughly, and powders or fine granules are formulated form the mixture.

Formulation 3

| Ingredient | Part |
|---|---|
| Compound of the formula (I) | 1 |
| Surface active agent | 5 |
| Physiological saline | 94 |

The above ingredients are mixed under heating, and dispensed under sterile conditions into ampoules to obtain injections.

What is claimed is:

1. N-Acylpyrrolidine derivatives of the general formula (I):

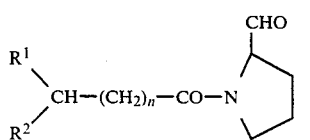

wherein $R^1$ is a hydrogen atom, a $C_{1-4}$ alkyl group or the phenyl group, with the proviso that
when $R^1$ is a hydrogen atom, $R^2$ is phenoxy, benzoyl, the phenyl group, or a phenyl group which is mono-substituted by a halogen atom or a $C_{1-4}$ alkoxy group, and that
when $R^1$ is a $C_{1-4}$ alkyl group or the phenyl group, $R^2$ is an aralkyl group of 7 to 10 carbon atoms, a $C_{1-4}$ alkyl group, the phenyl group or a phenyl group mono-substituted by a halogen atom or a $C_{1-4}$ alkoxy group; or $R^1$ and $R^2$ together form an unsubstituted benzylidene group or a benzylidene group mono-substituted by a $C_{1-4}$ alkoxy group; and
n is an integer of 0 to 5.

2. The compound according to claim 1 wherein $R^1$ is a hydrogen atom, $R^2$ is methoxyphenyl, chlorophenyl, phenoxy or benzoyl and n is an integer of 0 to 2.

3. The compound according to claim 1 wherein $R^1$ is the phenyl group or a $C_{1-4}$ alkyl group and wherein n is an integer of 0 to 2.

4. The compound according to claim 1 wherein $R^1$ is a $C_{1-4}$ alkyl group, $R^2$ is phenethyl and wherein n is 0.

5. A compound according to claim 1 wherein $R^1$ and $R^2$ together form a methoxybenzylidene group.

6. A pharmaceutical composition comprising a N-acylpyrrolidine derivative of the formula (I):

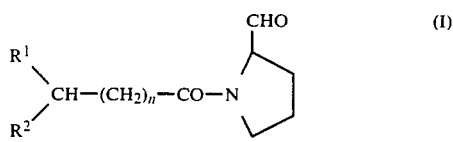

wherein $R^1$ is hydrogen atom, a $C_{1-4}$ alkyl group or the phenyl group, with the proviso that
when $R^1$ is a hydrogen atom, $R^2$ is phenoxy, benzoyl, the phenyl group, or a phenyl group which is mono-substituted by a halogen atom or a $C_{1-4}$ alkoxy group, and that
when $R^1$ is a $C_{1-4}$ alkyl group or the phenyl group $R_2$ is an aralkyl of 7-10 carbon atoms, a $C_{1-4}$ alkyl group, the phenyl group or a phenyl group which is mono-substituted by a halogen atom or a $C_{1-4}$ alkoxy group; or $R^1$ and $R^2$ together form an unsaturated benzylidene group or a benzylidene group which is mono-substituted by a $C_{1-4}$ alkoxy group; and
n is an integer of 0 to 5, which N-acylpyrrolidine derivative is present in an amount effective for treating amnesia, together with a pharmaceutically acceptable carrier.

7. A pharmaceutical composition according to claim 6 wherein the amount of said N-acylpyrrolidine derivative of the formula (I) is 0.1 to 90% by weight of the total composition.

8. A pharmaceutical composition according to claim 7 wherein the amount of said N-acylpyrrolidine derviative of the formula (I) is 1 to 45% by weight of the total composition.

9. A pharmaceutical composition according to claim 6 which composition is in a form suitable form oral administration.

10. A pharmaceutical composition according to claim 6 which composition is in a form suitable for parenteral administration.

* * * * *